United States Patent [19]

Thomsen

[11] Patent Number: 4,711,631
[45] Date of Patent: Dec. 8, 1987

[54] ARRANGEMENT FOR JOINING DENTURE COMPONENTS BY ADHESION (DEVICE FOR BINDING PARTS OF DENTAL PROSTHESIS BY ADHESION)

[76] Inventor: Peter K. Thomsen, Wiesenweg 7, 2300 Molfsee/Schulensee, Fed. Rep. of Germany

[21] Appl. No.: 756,971
[22] PCT Filed: Nov. 2, 1984
[86] PCT No.: PCT/EP84/00348
 § 371 Date: Jun. 28, 1985
 § 102(e) Date: Jun. 28, 1985
[87] PCT Pub. No.: WO85/01872
 PCT Pub. Date: May 9, 1985

[30] Foreign Application Priority Data

Nov. 4, 1983 [DE] Fed. Rep. of Germany ....... 3340016
Sep. 4, 1984 [DE] Fed. Rep. of Germany ....... 3432486

[51] Int. Cl.[4] .............................................. A61C 13/22
[52] U.S. Cl. ................................................... 433/181
[58] Field of Search ........................ 433/181, 182, 183

[56] References Cited

U.S. PATENT DOCUMENTS 1,471,754 10/1923 Rosenblum ..................... 433/181
2,617,194 11/1952 Clark .............................. 433/209
4,362,509 12/1982 Sule ................................. 433/181
4,380,436 4/1983 Kipp ................................ 433/182

Primary Examiner—Robert Peshock
Attorney, Agent, or Firm—Chilton, Alix & Van Kirk

[57] ABSTRACT

Arrangement for joining denture components by adhesion, in particular a prosthesis component with an anchoring or bedding part. It consists of a pair of connecting elements or model parts for connecting elements which are joined to or can be joined to the components to be joined and at least one of which encloses the other. So that the join can be closed without the danger of thermal distortion with correctly prepared individual components—if appropriate even in the mouth of the patient—the surfaces to be joined on the connecting elements or the model parts have an intermediate space which allows positioning of the components to be joined and can be filled with sealing compound which hardens, the surfaces comprising surface portions cut away in respect of the direction of loosening and hence acting on the sealing compound in a positive manner. To shape the intermediate space, a particular model part is envisaged, which can be inserted, in identical shape, between a model part for the internal connecting element and a model part for the external connecting element.

12 Claims, 11 Drawing Figures

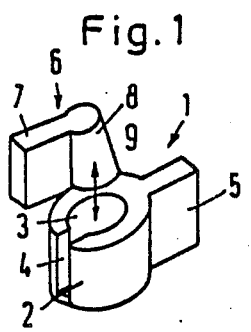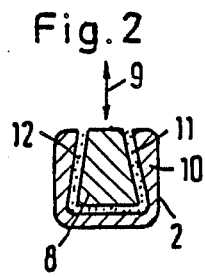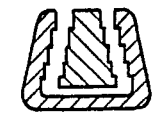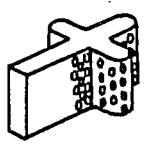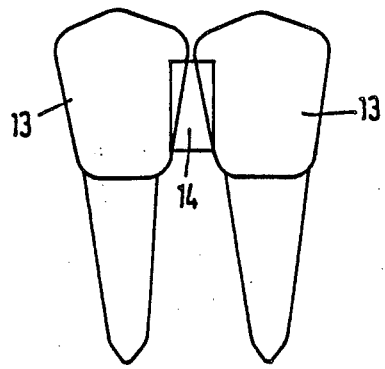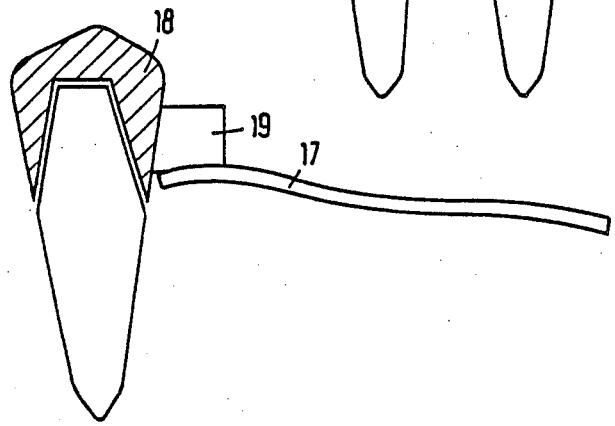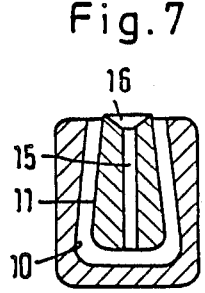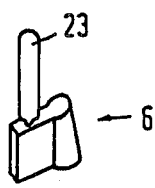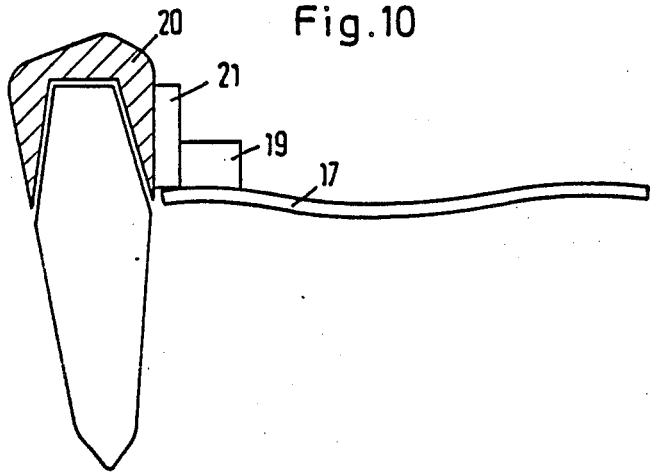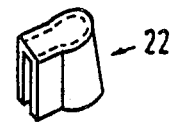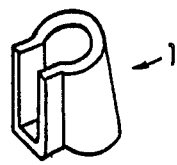

ARRANGEMENT FOR JOINING DENTURE COMPONENTS BY ADHESION (DEVICE FOR BINDING PARTS OF DENTAL PROSTHESIS BY ADHESION)

DESCRIPTION

The invention relates to an arrangement for joining denture components which are to be located laterally with respect to one another, in particular a prosthesis component with an anchoring or bedding part, by adhesion, consisting of a pair of connecting elements or model parts which are joined to or can be joined to the components to be joined, at least one of which encloses the other.

By denture components which are to be located laterally with respect to one another there are to be understood those which, in a projection on the bite plane, lie at different points (not on top of one another). The joining of such denture components therefore presents problems, because on the one hand the laterally displaced denture components are exposed to forces of different strength and acting in different directions and the joint therefore has to take up forces of the most diverse nature and direction (including flexural and tensile forces), and because on the other hand the joint must exactly fulfil the fitting requirements which the joined denture components meet in the jaw.

In denture technology, it is frequently necessary for denture components which belong together to be produced separately, either because this is required due to the production or fitting technique or because, as prosthesis components which can be removed, it must also be possible to separate them from the fixed anchor during use.

In all of these cases, it is of extreme importance that their mutual joining exactly meets the dimensional conditions determined by the anchors or abutments present or by the shape of the jaw. In practice, great difficulties are encountered in meeting this requirement. On the one hand, even in the production of the individual components, tolerances cannot be reliably excluded on the path between impression and production of the finished cast component. On the other hand, conventional joining by soldering is a frequent reason for deformations because of the unavoidable heat expansions, which may differ. Other problems arise with this conventional joint in that stresses are caused during soldering which are "frozen" in the casting operation. Even if individual pieces which fit exactly, together with intermediate members, are soldered together to give, for example, an extended bridge, it is entirely possible for inaccuracies in fit to result from the soldering operation (Böttger, Gründler: "Das zahnärztliche and zahntechnische Vorgehen beim Teleskopsystem in der Prothetik (Dental and dentistry procedure in the telescopic system in prosthetics), Munich 1970, pages 73 and 110). In practice, such deformations are only too frequently not discovered or not taken into account by the dental technician or dentist and then become the source of great discomfort to the patient. Adhesive jonts have been disclosed to avoid these disadvantages (Geiger: "Geschiebetechnik" (Bedding Technique), page 167 et seq.). A secondary bedding component is here provided with an adhesive pin, whilst the prosthesis component to be joined is provided with a matching eye, which is shaped by shaping the model on the adhesive pin, coated with a thin layer of wax. The adhesive pin and eye essentially match one another in the same shape, i.e. the mutual position of the secondary bedding component and prosthesis component is determined by the surface portions of the adhesive peg and the eye to be connected by adhesion. Subsequent correction is not envisaged. Another disadvantage of the known technique is that the adhesive peg must first be modeled and cast before the component to be joined thereto can be modeled.

A false tooth is also known (German Offenlegungsschrift No. 2,247,649), which consists of a root section and a crown joined to one another via an elastomeric, optionally prefabricated intermediate layer. Because these components lie over one another in the projection at the occlusal plane and therefore essentially only pressure forces are transmitted, the intermediate layer does not have to be stuck and can therefore be prefabricated, cohesion against the small tensile forces to be expected resulting from the fact that a cut-away peg and a cut-away bore interact in a push-button like manner over the elastic intermediate layer. Although the elastomeric intermediate layer can be introduced as a liquid and allowed to harden, in this connection adhesion is neither necessary nor obvious. In the same connection, it is known to anchor the cut-away peg in a cylindrical bore of the root section by means of a cylindrical attachment via a suitable binder, clearance being provided to accommodate the binder. The size of this clearance is in fact unknown; however, since a quite centrally-seated arrangement of the crown in respect of the root section is desired, this clearance must be considered to be small in order to avoid unwanted inaccuracies.

The invention is based on the object of providing a joining arrangement of the type mentioned at the outset which allows joining of the denture components to give an accurate fit and subsequent reciprocal correction of the position following their individual production.

In the solution according to the invention, the surfaces to be joined on the connecting elements or model parts enclose an intermediate space which permits alignment of the components to be joined and can be filled or is filled with sealing compound which hardens, these surfaces acting in a positive manner on the sealing compound with portions of the surface which are cut away in respect of the loosening direction.

The clearance formed by the intermediate space between the connecting elements allows the individual components themselves to be joined together to fit accurately even if inaccuracies in respect of attachment of the connecting elements may have occurred during their individual production. These inaccuracies are accommodated by the clearance. So that this clearance is made possible, the invention is not content with adhesion, which would necessitate a small distance between the surfaces to be joined, but has as a condition a seal for filling the intermediate space. The cut-away shaping of the surfaces which are to be joined and which enclose one another thereby ensures that the head of the seal formed from the sealing compound by hardening is exposed only to pressure and shearing forces.

In this connection, the manner in which the sealing compound is introduced into the intermediate space is of no consequence. However, it may be advantageous to provide an injection attachment on the arrangement, i.e. a component suitable for attaching the opening of an injection apparatus for injection of the sealing compound, this component being connected, for example, to the space to be sealed via a bore. Instead of first combining the connecting elements in the free state and only then injecting the sealing compound, it is also possible for the sealing compound to be accommodated in the space formed by the external connecting element before the elements are combined, and then to insert the other element so that the sealing compound then completely and reliably fills the sealing space formed between the elements. So that the sealing compound is not forced out of an opening opposite the insertion opening in the external element when the internal element is inserted, without completely filling the intermediate space after insertion of the internal element, it may be appropriate in this connection to design the external element so that it is closed on the side opposite the insertion opening. This also has the advantage that the closed side of the external element can easily absorb the forces which are not absorbed by the cut-away surfaces of the two elements opposite one another.

A cold-hardening sealing compound, preferably a cold-hardening synthetic resin, amalgam or the like, is advantageously used. In particular, this results in a particular advantage of the invention that the joining can be carried out in the mouth of the patient by the dentist. With extended bridges, it has hitherto been necessary to produce a separate impression for joining together the individual components, but it was not possible to exclude joining inaccuracies here. The awkwardness and inaccuracies of the known process are avoided by the invention. However, if desired, it is of course also possible to make the joint according to the invention in the laboratory, and it appropriate also with sealing compounds which, because of some property or other, do not permit processing in the mouth of the patient, for example because of an increased sealing or hardening temperature or because of their toxicity in the monomeric state. The invention also includes the possibility of initially temporarily making the joint in the mouth of the patient by exposing the sealing compound to preliminary hardening to a degree such that the joined components can be removed again without mutual deformation, by applying appropriate care, after which the actual hardening—for example using elevated temperatures—is done in the laboratory.

The sealing compound chosen is advantageously a material which is rigid in the hardened state, so that a correspondingly rigid joint comparable to solder is achieved. If the joint is to be non-rigid to a certain degree, so that the connecting elements can give a little in the case of external application of force and are therefore at less risk of being overloaded, an elastic element is advantageously provided inside or outside the region of the joint, separately from the rigid sealing compound. For example, an elastic material can be applicable or can be applied to at least one of the connecting element surfaces facing one another, and the remaining space can be fillable with or filled with the sealing compound which hardens.

The connecting elements can be prefabricated in the material finally desired and joined to the components to be joined, for example, by soldering. Instead of this, it is of course also possible, in production of denture components by casting, to produce the connecting elements integrally with these components. Prefabricated model parts of wax or plastic are advantageously used for this, and are combined with the model parts of the denture components in the customary manner.

The shape chosen for the connecting elements in a section at right angles to the loosening direction can vary according to requirements, for example it can be bar-shaped, circular, oval-shaped, cross-shaped or star-shaped. Combinations of these or other shapes are also possible.

Apart from its joining function, the joining arrangement can also serve other purposes, for example as a bridge member or stump for accommodating a crown.

It is also possible for several joint according to the invention to be provided. Thus, it is also possible for the bedding part (primary bed, which is to be attached to a crown overdenture or similar anchor,) to be attached in the manner according to the invention.

As used herein, the term "denture" means the artificial replacement of one or more natural teeth and is closely related to the term "prosthesis", i.e. an artificial device to replace a part of the body. Bridgework should be understood to mean a partial denture held in place by anchorage to an adjacent tooth. Overdentures should be understood to mean dentures which rest or are mounted on a remaining root of a natural tooth. The term "applicance" should be understood to encompass dentures, prosthesis and bridgework. The term "denture component" should be construed broadly to refer to all or part of an artificial replacement tooth, whereas the term "joining element" or "model part" refers to structures utilized directly or indirectly to join or support the denture components.

The design of the intermediate space is of decisive importance for the success of the joint according to the invention. On the one hand, the distance between the surfaces to be joined should be as small as possible, so that the seal can develop properties similar to those of adhesion. On the other hand, the clearance must be sufficiently large to enable subsequent correction. Individual shaping could give rise considerable errors. The invention therefore provides for a particular model part made of wax or plastic for reproduction of the intermediate space. A corresponding model part made of plastic can also be provided for the internal connecting element. However, the model part for the intermediate space can also be used in connection with a metal part which has been prefabricated as the internal connecting element and is joined, for example, to a secondary bed. The model part for formation of the intermediate space is worthy of protection independently of the cut-away shape of the surfaces interacting on the connecting elements.

In most cases of application, the external connecting element can be individually modeled more easily than the internal element, so that a model part made of plastic is not absolutely necessary for the external connecting element. However, it may be advantageous also to use a model part made of plastic for this purpose, in particular to guarantee the minimum wall strength necessary for the required strength of the external connecting element.

The existence of a model part made of plastic for the internal connecting element and for the intermediate space and, if appropriate, also for the external connecting element enables the model parts to be waxed onto the denture models to be joined and thus at the same time to model these. They are then carefully separated from one another, for example by pulling the model part envisaged for reproduction of the intermediate space carefully out from between the model parts of the internal and external connecting elements. This results in the great advantage that the denture components to be joined can be modeled simultaneously, without it being necessary for one of the two to be already in the finished cast form during modeling of the other.

In a particularly preferred embodiment, the internal connecting element or model part includes a part thickened in a peg-like manner on a bar projecting therefrom in the joining direction, the direction of the peg running at right angles to the joining direction. The joining direction here is to be understood as the direction joining the denture components to be joined to one another. The peg direction envisaged at right angles to this allows the connecting elements to be positioned, separated and joined by means of parallel holders.

The external connecting element or model part is advantageously omega-shape in cross-section, the omega opening enclosing, as the bar opening, part of the bar, whilst the peg lies within the internal space also designed as the bar opening. The width of the bar opening is advantageously narrower than the thickness of the peg-like part measured in parallel. This means that the internal connecting element or model part can be inserted with its thickened peg not through the bar opening but through an insertion opening at one end of the external connecting element or model part, the insertion direction being at right angles to the connecting direction. The end opposite the insertion opening is at least partly closed, so that the sealing compound introduced into the external connecting element or model part before insertion of the internal connecting element or model part is held therein during joining and so that forces acting in the direction of this end are absorbed. The external connecting element or model part is thereby given the shape of a beaker, which has a slit in the side to form the bar opening and which narrows, preferably conically, towards its opening complementarily to the shape of the peg of the internal connecting element or model part.

The intermediate space model part is advantageously also closed at one end in the shape of a beaker with a slit in the side, and in particular at its narrower end corresponding to the insertion opening of the external connecting element, so that it can be pulled out after modeling of the external model part. For this purpose, it should have a wall thickness which is constant or becomes thinner from its closed end to the other open end. During this pulling out, either the intermediate space model part or the external model part must undergo slight elastic deformation. So that this is possible, the intermediate space model part and/or the external model part should be elastically non-rigid. All the model parts should fit into one another exactly so that they take up a defined position during modeling.

The invention is explained below in more detail with reference to the drawing, which illustrates embodiment examples. In the figures:

FIG. 1 shows the perspective view of a pair of connecting elements,

FIGS. 2–5 show sections through different embodiments of connecting elements,

FIG. 6 shows a connecting element which is cross-shaped in cross-section,

FIG. 7 shows a section through another embodiment,

FIG. 8 shows the use of the joining arrangement between two crowns,

FIG. 9 shows the joining arrangement between a telescopic anchor and a model cast skeleton, FIG. 10 shows an arrangement similar to FIG. 9 between the bed of a crown and a model cast skeleton, and FIG. 11 shows a broken down perspective view, similar to FIG. 1, of associated model parts of the internal and external connecting element of the intermediate space.

FIG. 1 shows an external connecting element 1, which contains, within an enclosing part 2, a hollow space 3, which is open in a slit manner at 4 and widens conically from the top opening which can be seen in FIG. 11 to its bottom. The enclosing part 2 is joined to a bar 5 which is used for connection to a denture component. If appropriate, it can also be dispensed with. The internal connecting element 6 has on a bar 7 corresponding to the bar 5 a conical peg 8, the maximum diameter of which is somewhat less than the opening diameter of the space 3. The width of the slit 4 is somewhat greater than the thickness of the bar 7. If the two elements are joined together in the direction of the arrow 9, which designates the joining and loosening direction as the longitudinal direction of the space 3 and the peg 8, there is still a certain clearance between these two parts, so that the connecting parts 1 and 6 are movable within a tolerance range, the size of which, although as small as possible, is great enough so that the measurement tolerances which occur in practice can be accommodated. The bar advantageously extends over essentially the entire height of the peg 8.

FIG. 2 illustrates a longitudinal section through the parts 2 and 8 inserted into one another, the sealing compound which fills the hollow space between the two being shown as dots. The inner surface 10 of the part 2 and the outer surface 11 of the part 8 are parallel and conical, so that they have surface portions which face one another in a projection direction corresponding to the loosening direction 9 and run at right angles to the direction 9. By means of the sealing compound 12, they are therefore joined together in a positive manner, the latter being subjected merely to pressure and shearing forces but not to tensile forces, so that the gluing or adhesion forces existing between the surfaces of parts 2 and 8 on the one hand and the sealing compound on the other hand are of no consequence.

FIGS. 3–5 show longitudinal sections, corresponding to FIG. 2, with arrangements of other shapes, the surface portions of the surfaces 10 and 11 directed against the direction of loosening and against one another each being somewhat different. The external and internal elements of these embodiment examples can be freely combined with one another.

The full extent of the outer and inner surfaces do not have to be complementary in shape detail, although this is advantageous, so long as at least a portion of the outer surface has a shape complementary to the undercut whereby a positive interaction arises between the complementary surface and a portion of the undercut through the application of a compressing force on the sealing compound, to prevent loosening therebetween.

In the embodiment example according to FIG. 6, a cross-shaped cross-section which deviates from the circular cross-section shown in FIG. 1 is represented. The hollow space provided in the associated element, not shown, can also have a cross-shaped cross-section. As already mentioned, other cross-sections are furthermore also possible.

The surface of the element shown in FIG. 6 is provided with a large number of burls for the purpose of positive interaction with the sealing compound.

FIG. 8 shows two crowns 13, which can also be part crowns or inlays, joined together by a joining arrangement shown schematically at 14. This joining arrangement should be according to the invention, for example in the form of one of the embodiments according to FIGS. 1–6. This obviously has the advantage that the crowns 13 are only joined to one another when finally placed on the tooth stump. This ensures that each individual crown fits securely, independently of any errors in the dimensional accuracy of their joint which could have occurred if this had first been made in the laboratory. Parallelity defects in the tooth stumps can also be compensated.

FIG. 7 illustrates how such a join can be made at the location. The figure shows within the internal connecting element a bore 15, which ends at the top in a hollow cone 16. After the connecting elements have been combined, an injection apparatus can be placed on this hollow cone, as an injection attachment, for injecting the sealing compound, which flows down through the bore 15 and upwards again through the hollow space between the surfaces 10 and 11, until it completely fills the hollow space. Instead of this, it would also be possible to fill the hollow space formed in the external element about half-full with the sealing compound and then to insert the internal connecting element, which displaces the sealing compound to the extent that is completely fills the hollow space.

FIGS. 9 and 10 illustrate the use of the joining arrangement according to the invention for joining a model cast skeleton as part of a detachable prosthesis with the associated anchor. In FIG. 9, the anchor is designed as a telescopic crown 18. The joining arrangement shown schematically only in outline at 19 is therefore joined on the one hand to the crown 18 and on the other hand to the model cast skeleton 17. The joining arrangement in this embodiment example is prefeably closed and allowed to harden after the prosthesis components have been matched in respect of depth in the mouth of the patient.

The embodiment according to FIG. 10 differs from that according to FIG. 9 in that the crown 20, which in this case is fixed, is not used as the telescopic portion of the anchor, and instead a bed 21 located thereon is used. The joining arrangement 19 according to the invention is therefore located between the bed 21 and the model cast skeleton 17, it also being possible for the bedding part on or in the crown to be joined according to the invention.

In both cases, due to the replacement of the conventional soldered join by the joining arrangement according to the invention, there is the advantage that the joint can be concluded in the mouth of the patient (if appropriate also on an impression) after correct preparation of the individual components, without the danger of thermal distortion.

The joining arrangement can in both cases be designed externally as a bridge member or stump for accommodating a crown etc.

In connection with the embodiment examples, the case has been described where the joint comprises in each case only one space which can be filled with sealing compound, ie. a pair of projections/depressions which engage in one another. If this is advantageous, however, a larger number of pairs of projections/depressions, ie. components which engage, can be provided on the two components to be joined, each associated pair of which forms in each case a space which can be filled or is filled with the sealing compound. In this case, not only is one space fillable or filled with the sealing compound, but several spatially separate such spaces exist.

In the previous example, the question of whether the components are finished metallic connecting elements or model parts for the production has been left open. For example, in the case of FIG. 10, it is conceivable that the secondary bedding part 21 together with the internal connecting part 6 is a one-piece, ready-to-use unit which is commercially available as such and which is provided with an intermediate space model part 22 (FIG. 11), which is placed on top, to fit accurately, and onto which the model skeleton 17 can be modeled, with or without the use of an external model part 1 (FIG. 11).

In Example 9, it is conceivable that part 18 is a telescopic crown onto which the model part 6 (FIG. 11) is waxed, onto which, in turn, the intermediate space model part 22 is placed and, if appropriate, is fixed thereon with secondary adhesive, and that the model skeleton 17 is modeled thereon, with or without model part 1, to form the external connecting element.

The internal connecting element is usually employed with the thin end of the conical peg at the bottom, especially if the forces affecting the joint chiefly act basally on the side of the internal connecting element and chiefly act occlusally on the external connecting element. However, depending on the direction of action of the force, the conical peg can also be used with the pointed end directed occlusally. In the latter case, assembly is carried out with the parallel holder 23 shown in FIG. 11, whilst in the other case the parallel holder 23 shown in removed and a parallel holder, not shown, provided on the opposite side of the model part is used instead.

The intermediate space model part 22 is closed at the end which appears at the top in FIG. 11, in order to form a buffer used for correct placing on the internal model part 6. If the intermediate space model part is placed on the internal model part 6 and is fixed thereto by means of an adhesive, the closed side can be removed if space conditions necessitate or permit.

In contrast, the external model part 1 in FIG. 11 is shown closed on the underside. This means that it must be placed with its thinner end over the thicker end of the intermediate space model part 22. For this purpose, it is correspondingly elastically non-rigid in design. Such non-rigidity of the intermediate space model part 22 and/or the external model part 1 is also necessary if the intermediate space model part 22 is to be pulled out from between the internal and the external model part to separate the modeled pieces. The non-rigidity and elasticity of polyethylene, especially high pressure polyethylene, for example, has proved suitable.

The surfaces of the connecting elements must be clean and free from grease before final joining together. They can be cleaned out, for example with a fine jet apparatus, and, if appropriate, roughened. The denture components to be joined are then placed on the model or in the final position on the jaw and, after the external connecting element has been filled with the sealing compound, are lowered into their end position.

After the compound has been hardened, the excess is ground off and, if appropriate, the pieces are finished.

A two-component plastic of low shrinkage is advantageously used as the sealing compound. Experiments have shown that the strength of the joint according to the invention entirely meets the requirements of dentistry.

In the example of FIG. 8, it is possible for an external model part 1 to be incorporated into each crown model and for a two-sided joining element to be present, which consists of a bar with pegs 6 provided on both ends, and each peg can interact with and be stuck to one of the joining elements 1 shaped in the crowns. The two-sided joining element can be supplied in ready-to-use form made of a suitable metal. It can also have a limited elasticity, in the manner described above.

I claim:

1. An arrangement for joining denture components to be located laterally with respect to one another comprising:
    a pair of joining elements (1,6) each one of the elements being connectable at one end to one of the components to be joined, and joined at their other ends to each other by interengagement of an internal part having an outer surface (11) and an external part having an inner surface (10), at least a portion of the inner surface being undercut with respect to the joining and loosening direction and at least a portion of the outer surface having a shape complementary to the undercut, the engagement of the internal and external parts enclosing an intermediate space (12) therebetween which permits adjustment of the components to be joined (13; 17, 18; 17, 21) during assembly of the arrangement, the intermediate space being filled with a hardening sealing compound, whereby after the compound has hardened, the inner and outer surfaces act in a positive manner to apply a compressive force on the sealing compound against the portions of the surface which are undercut in respect of the loosening direction to prevent loosening therebetween.

2. An arrangement as claimed in claim 1, further including means (16) for injecting sealing compound into said intermediate space.

3. An arrangement as claimed in either of claims 1 or 2, wherein a cold-hardening sealing compound is used.

4. An arrangement as claimed in claim 1, wherein the internal part (8) includes a part (8) thickened in a peg-like manner on a bar projecting therefrom in the joining direction, the direction of the peg running at right angles to the joining direction.

5. An arrangement as claimed in claim 4, wherein the external part (1) surrounds the peg (8) and is omega-shaped in cross-section, with a bar opening-part of the bar (7).

6. An arrangement as claimed in claim 4, wherein the width of the bar opening of the external part (1) is narrower than the thickness measured parallel to this opening, of the peg-like part (8) and has an insertion opening for the peg-like part (8) at one end.

7. An arrangement as claimed in any one of claims 12 and 17, wherein the receptacle part (1) and the peg-like part (8) are cut away in relation to the opening.

8. An arrangement as claimed in any one of claims 12 and 17 wherein the receptacle (1) is at least partly closed at one end.

9. An arrangement as claimed in female part (1).

10. An arrangement as claimed in claim 9 wherein the intermediate space model part (22) has a wall thickness which remains constant or becomes thinner from its closed end to the other, open end, so that it can be pulled out between the male and female parts.

11. An arrangement as claimed in claim 5 wherein the intermediate space model part (22) and/or the joining element model part are elastically non-rigid.

12. An arrangement for joining denture components laterally with respect to one another, comprising:
    an anchoring denture component;
    a supported denture component laterally adjacent the anchoring component;
    a first joining element affixed to one of the anchoring or supported components and having a female part extending laterally therefrom, the female part having an inner surface defining an open ended, undercut, hollow receptacle oriented substantially vertically to the lateral direction;
    a second joining element affixed to the other of said anchoring or supported components and having a male part extending laterally therefrom, the male part having a plug defining an outer surface having at least a portion complementary to said undercut inner surface, the plug being engaged with the receptacle with clearance to provide an intermediate space between said inner and outer surfaces; and
    a hardened sealing compound occupying the intermediate space, for immobilizing the male portion relative to the female portion in the lateral and vertical directions, whereby stress on the joining elements in the direction tending to pull apart the plug and the receptacle, will impart a compressive force on the portion of said hardened sealing compound occupying the intermediate space along said undercut, thereby preventing pulling apart of the plug from the receptacle.

* * * * *